(12) United States Patent
Green

(10) Patent No.: US 9,486,132 B2
(45) Date of Patent: Nov. 8, 2016

(54) ACCESS DEVICE FOR ACCESSING TISSUE

(71) Applicant: Abbott Cardiovascular Systems, Inc., Santa Clara, CA (US)

(72) Inventor: Michael Lee Green, Pleasanton, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 208 days.

(21) Appl. No.: 13/744,203

(22) Filed: Jan. 17, 2013

(65) Prior Publication Data

US 2014/0200409 A1    Jul. 17, 2014

(51) Int. Cl.
| | | |
|---|---|---|
| *A61B 17/32* | (2006.01) | |
| *A61B 1/32* | (2006.01) | |
| *A61B 17/00* | (2006.01) | |
| *A61B 17/064* | (2006.01) | |
| *A61B 17/08* | (2006.01) | |
| *A61B 17/02* | (2006.01) | |

(52) U.S. Cl.
CPC ............. *A61B 1/32* (2013.01); *A61B 17/0057* (2013.01); *A61B 17/064* (2013.01); *A61B 17/083* (2013.01); *A61B 17/0293* (2013.01); *A61B 2017/00659* (2013.01); *A61B 2017/00668* (2013.01); *A61B 2017/0641* (2013.01); *A61B 2017/0645* (2013.01)

(58) Field of Classification Search
CPC .................. A61B 1/267–1/2763; A61B 1/32; A61B 17/085; A61B 17/10; A61B 17/105; A61B 17/32; A61B 2017/081; A61B 2017/086; A61B 2017/088; A61B 17/03; A61B 2017/00619; A61B 2017/00623; A61B 17/122; A61B 17/1227; A61B 17/08–17/083; A61B 17/0057; A61B 2017/00584–2017/00592; A61B 2017/00641; A61F 2/442

USPC ......... 600/201–249; 606/213, 215–221, 120, 606/151, 157–158; 623/2.36

See application file for complete search history.

(56) References Cited

U.S. PATENT DOCUMENTS

| | | | | |
|---|---|---|---|---|
| 2,238,563 | A * | 4/1941 | Jacques .......................... | 27/21.1 |
| 4,250,882 | A * | 2/1981 | Adair ............................ | 604/355 |
| 5,429,121 | A * | 7/1995 | Gadelius ....................... | 600/217 |
| 5,704,901 | A * | 1/1998 | Meister ......................... | 600/243 |
| 5,779,707 | A * | 7/1998 | Bertholet et al. ............... | 606/75 |
| 6,277,140 | B2 * | 8/2001 | Ginn et al. .................... | 606/213 |
| 6,620,098 | B1 * | 9/2003 | Milverton ..................... | 600/236 |
| 7,018,332 | B1 * | 3/2006 | Masson et al. ............... | 600/227 |
| 7,022,069 | B1 * | 4/2006 | Masson et al. ............... | 600/217 |
| 7,229,408 | B2 * | 6/2007 | Douglas et al. .............. | 600/214 |
| 7,597,706 | B2 * | 10/2009 | Kanner et al. ................ | 606/219 |
| 8,388,525 | B2 * | 3/2013 | Poo et al. ..................... | 600/206 |
| 8,540,628 | B2 * | 9/2013 | O'Prey et al. ................ | 600/208 |
| 8,597,181 | B1 * | 12/2013 | Sasaki .......................... | 600/208 |
| 8,602,983 | B2 * | 12/2013 | Kleyman ...................... | 600/208 |
| 8,603,116 | B2 * | 12/2013 | Roorda ......................... | 606/151 |
| 8,672,953 | B2 * | 3/2014 | Reyes et al. .................. | 606/142 |
| 8,777,849 | B2 * | 7/2014 | Haig et al. .................... | 600/206 |
| 2002/0002324 | A1 * | 1/2002 | McManus ..................... | 600/208 |

(Continued)

*Primary Examiner* — Eduardo C Robert
*Assistant Examiner* — Michelle C Eckman
(74) *Attorney, Agent, or Firm* — Workman Nydegger; Randy Shen

(57) ABSTRACT

A clip is provided for managing access through tissue. The clip is placed around an opening in tissue, although the opening may alternatively be formed after the clip is deployed. The clip can expand when medical devices are introduced through the clip and through the opening. When the medical devices are removed, the clip closed automatically to substantially close the opening.

24 Claims, 10 Drawing Sheets

(56) References Cited

U.S. PATENT DOCUMENTS

| | | | |
|---|---|---|---|
| 2002/0002401 A1* | 1/2002 | McGuckin et al. | 623/1.19 |
| 2002/0032454 A1* | 3/2002 | Durgin | A61B 17/10 |
| | | | 606/151 |
| 2002/0065451 A1* | 5/2002 | Spence et al. | 600/201 |
| 2002/0107542 A1* | 8/2002 | Kanner et al. | 606/213 |
| 2003/0032981 A1* | 2/2003 | Kanner et al. | 606/219 |
| 2004/0093024 A1* | 5/2004 | Lousararian et al. | 606/213 |
| 2004/0138533 A1* | 7/2004 | Spence et al. | 600/201 |
| 2004/0267312 A1* | 12/2004 | Kanner et al. | 606/219 |
| 2005/0277959 A1* | 12/2005 | Cosgrove | A61B 17/12 |
| | | | 606/151 |
| 2006/0004261 A1* | 1/2006 | Douglas | 600/210 |
| 2006/0106416 A1* | 5/2006 | Raymond et al. | 606/198 |
| 2006/0149137 A1* | 7/2006 | Pingleton et al. | 600/208 |
| 2006/0212114 A1* | 9/2006 | Menicanti et al. | 623/2.36 |
| 2007/0027364 A1* | 2/2007 | Schwer | 600/219 |
| 2007/0060951 A1* | 3/2007 | Shannon | A61B 17/122 |
| | | | 606/216 |
| 2007/0083229 A1* | 4/2007 | Deutsch | 606/213 |
| 2007/0238933 A1* | 10/2007 | Alinsod et al. | 600/231 |
| 2008/0033251 A1* | 2/2008 | Araghi | 600/235 |
| 2008/0234550 A1* | 9/2008 | Hawkes et al. | 600/204 |
| 2008/0249474 A1* | 10/2008 | Baker | 604/167.02 |
| 2009/0093850 A1* | 4/2009 | Richard | 606/300 |
| 2009/0171380 A1* | 7/2009 | Whiting | 606/158 |
| 2009/0203967 A1* | 8/2009 | Branch et al. | 600/210 |
| 2010/0125164 A1* | 5/2010 | LaBombard | 600/104 |
| 2010/0145153 A1* | 6/2010 | Rioux et al. | 600/208 |
| 2010/0228269 A1* | 9/2010 | Garrison et al. | 606/139 |
| 2010/0274091 A1* | 10/2010 | Rothstein et al. | 600/201 |
| 2010/0312063 A1* | 12/2010 | Hess et al. | 600/204 |
| 2010/0312259 A1* | 12/2010 | Houser et al. | 606/142 |
| 2011/0054521 A1* | 3/2011 | Ventura et al. | 606/216 |
| 2011/0087249 A1* | 4/2011 | Rodrigues et al. | 606/151 |
| 2011/0092766 A1* | 4/2011 | Monassevitch et al. | 600/104 |
| 2011/0144661 A1* | 6/2011 | Houser et al. | 606/142 |
| 2011/0152888 A1* | 6/2011 | Ho et al. | 606/143 |
| 2011/0190578 A1* | 8/2011 | Ho et al. | 600/104 |
| 2011/0201893 A1* | 8/2011 | O'Prey et al. | 600/208 |
| 2011/0201896 A1* | 8/2011 | O'Prey et al. | 600/228 |
| 2011/0230900 A1* | 9/2011 | Sarradon | 606/151 |
| 2011/0288529 A1* | 11/2011 | Fulton | 604/510 |
| 2011/0319719 A1* | 12/2011 | O'Prey et al. | 600/206 |
| 2012/0016410 A1* | 1/2012 | Belson | A61B 17/085 |
| | | | 606/213 |
| 2012/0035630 A1* | 2/2012 | Roorda | 606/155 |
| 2012/0059394 A1* | 3/2012 | Brenner et al. | 606/142 |
| 2012/0157785 A1* | 6/2012 | Kleyman | 600/208 |
| 2012/0220833 A1* | 8/2012 | Ehrenreich | A61B 17/02 |
| | | | 600/219 |
| 2012/0245603 A1* | 9/2012 | Voss | 606/151 |
| 2012/0289785 A1* | 11/2012 | Albrecht et al. | 600/208 |
| 2012/0310261 A1* | 12/2012 | Cummins et al. | 606/158 |
| 2013/0012782 A1* | 1/2013 | Stearns et al. | 600/202 |
| 2013/0018228 A1* | 1/2013 | Armstrong | 600/204 |
| 2013/0018229 A1* | 1/2013 | Jaworek | 600/206 |
| 2013/0109924 A1* | 5/2013 | Gan | 600/205 |
| 2013/0150681 A1* | 6/2013 | O'Prey et al. | 600/206 |
| 2014/0039271 A1* | 2/2014 | Ehrenreich | 600/217 |
| 2014/0039525 A1* | 2/2014 | Trask | 606/142 |
| 2014/0039549 A1* | 2/2014 | Belsky | A61B 17/0057 |
| | | | 606/215 |
| 2014/0051935 A1* | 2/2014 | Kleyman | 600/208 |
| 2014/0081318 A1* | 3/2014 | Houser et al. | 606/213 |
| 2014/0194698 A1* | 7/2014 | Melsheimer et al. | 600/233 |
| 2014/0200409 A1* | 7/2014 | Green | 600/208 |

* cited by examiner

ACCESS DEVICE FOR ACCESSING TISSUE

BACKGROUND

1. The Field of the Invention

Embodiments of the invention relate generally to medical devices. More particularly, embodiments of the invention relate to medical devices for managing access in body tissue and/or body lumens.

2. The Relevant Technology

Catheterization and interventional procedures, such as angioplasty or stenting, are generally performed by inserting a hollow needle through a patient's skin and tissue into the patient's vascular system. A guide wire may be advanced through the needle and into the patient's blood vessel accessed by the needle. The needle is then removed leaving the guide wire in place, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. The introducer sheath may facilitate introducing various devices into the vessel, while minimizing trauma to the vessel wall and/or minimizing blood loss during a procedure. As the various devices are introduced through the introducer sheath, the opening or access site formed in the vessel may be subjected to additional trauma or tearing during the medical procedure.

Upon completing the procedure, the devices and introducer sheath are removed, leaving a puncture site or opening in the vessel wall. Traditionally, external pressure would be applied to the puncture site until clotting and wound sealing occur; however, the patient must remain bedridden for a substantial period after clotting to ensure closure of the wound. This procedure, however, may be time consuming and expensive, requiring as much as an hour of a physician's or nurse's time. It is also uncomfortable for the patient and requires that the patient remain immobilized in the operating room, catheter lab, or holding area. In addition, the insertion and removal of various medical devices can lead to problems at the access site.

BRIEF SUMMARY

Embodiments of the disclosure relate to managing access to tissue or to body lumens. Embodiments of the invention relate more particularly to an access device that controls access to openings formed in the tissue. In one embodiment, the access device includes a body having an interior edge and an exterior edge. The access device also includes an engagement mechanism that extends from the body. The engagement mechanism engages or attaches to the tissue. The body is configured to deform from a first position to a second position while the engagement mechanism is engaged with the tissue. The device may be bi-modal and be configured to hold both a first position (closed) and a second position (e.g., open) without an external bias.

In another embodiment, the access device manages access to tissue and can reduce trauma to the opening formed in the tissue. In this example, the access device includes a body. The body includes a first portion and a second portion joined at a fold. The first portion and the second portion are typically set in a first position and configured to deform to a second position. When deforming to the second position, an interior of the clip defined by the first and second portions effectively enlarges by, for example, elastic deformation to allow medical devices access to the opening. The access device includes a plurality of prongs that extend from the first and second portions. The first and second portions engage the tissue around the opening and attach the body to the tissue. The prongs can extend from either an interior or exterior edge of the access device's body.

In operation, a method for managing tissue often begins by forming an opening in the tissue. An access device is then placed or attached to the tissue around the opening, although the access device can be placed before the opening in the tissue is formed. The access device engages the tissue. During the procedure, the access device can be expanded to allow access to the opening. Through the interior of the access device, medical devices can be introduced through the opening. When the medical devices are removed, the access device returns to its original position and, because the access device is attached to the tissue, substantially closes the opening in the tissue.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which at least some of the advantages and features of the invention can be obtained, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF EMBODIMENTS OF THE INVENTION

Figure 1:
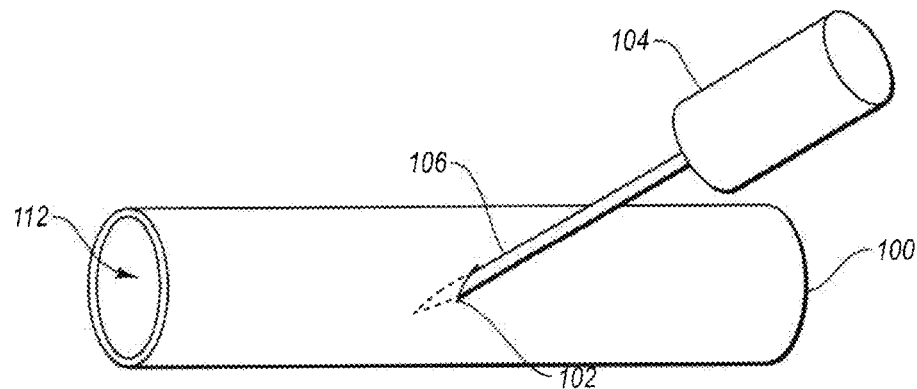
FIG. 1 shows an illustrative view of a medical device used to access a body lumen through an opening in a vessel to perform a medical procedure.

Embodiments of the invention relate to an access device, such as a clip, used in managing access to and/or through tissue. In many medical procedures, it is often necessary to create an opening or an access site in tissue for various reasons, including to introduce medical devices into the tissue or into body lumens. For example, an opening is often formed in a body lumen, such as a vessel, by puncturing the vessel. After the opening is formed in the vessel, the same opening is used to access the vessel lumen with other medical devices.

Although embodiments of the invention are discussed with reference to a vessel, one of skill in the art can appreciate, with the benefit of the present disclosure, that embodiments of the invention can also be used in conjunction with other tissue, lumens, and/or with other procedures. In general, embodiments of the invention relate to methods and devices for managing access to body lumens.

Embodiments of the invention relate to an access device (also referred to herein as a clip), that may be placed around the opening formed in the vessel. In one example, the clip is placed in or on the vessel before the opening is formed. In other words, the clip is configured for pre-puncture deployment. In one example, the clip can be configured to close the puncture at least temporarily in addition to being configured for reducing or minimizing trauma to the vessel.

For instance, the clip may reduce or minimize tearing that may occur at the opening during the insertion and/or removal of medical devices such as an introducer sheath or for other reasons. Minimizing trauma to the vessel, by way of example only, can improve recovery time, keep the size of the opening to a minimum, and make the procedure easier to perform.

The clip typically engages at least some of the tissue surrounding the opening in the tissue. Should a tear in the opening occur, the extent of the tear may be minimized because the clip may prevent the tear from expanding past the boundaries of the clip. In order to allow the medical procedure to be performed, the clip is usually deformable and/or expandable from a closed position to an expanded position. This enables additional or larger medical devices to be introduced. The clip typically is biased, whether mechanically or materially, i.e. by being a shape memory material, however, and automatically moves toward and/or to the closed position when possible. Alternatively, the clip may be bi-modal and configured to remain in either an open or closed position. In this example, the clip can transition to either position.

The clip may also be configured to snap to a closed position and snap to an open position. In other words, the clip may be configured to exist in both the closed position and in the open position without any external force. The clip may be formed such that when a force is applied to open the clip, the clip snaps to the open position. Similarly, the clip may snap to the closed position as well. In this case, the body of the clip is configured either mechanically and/or materially to bias the clip to both the open position and the closed position—no external bias is needed to keep the clip in either the open or closed position. The sides of the clip may be angled, for instance, and have a point at which the clip snaps to one position or the other position. Forcing the clip, or portion thereof, past the point causes the clip to snap to the other position.

In another example, a locking or holding mechanism may be used in at least some of the embodiments disclosed herein to keep the clip in either an open position or a closed position. The locking or holding mechanism can lock or hold the clip in an open position and/or hold the clip in a closed position.

Generally, the clip is configured to keep the opening closed. When a medical device needs to be introduced through the opening, the clip can be deformed or expanded or opened to allow entry of the medical device. When the medical device is removed, the clip is biased toward its original form or closed. Often, contraction of the clip can at least partially close the opening in the vessel.

The clip includes engagement mechanisms that can engage the vessel wall (or other tissue) around the opening. The engagement mechanisms allow the clip to be attached to the vessel wall. In some instances, the clip can also be shaped or contoured to accommodate the shape or contours of the body lumen. For example, the clip may be shaped to conform to the outer surface of the lumen. When a medical device (e.g., an introducer sheath or catheter) needs to be introduced, the clip can be expanded to enable introduction of the medical device via the opening. When the medical device is withdrawn from the opening, the clip moves toward to its previous shape, closing the opening in the vessel in some examples. Embodiments of the clip or access device disclosed herein may include features from any of the other embodiments or Figures discussed herein.

FIG. 1 shows an illustrative view of a medical device used to access a body lumen, such a blood vessel, through an opening in the body lumen to perform a medical procedure. In FIG. 1, the medical procedure includes forming a puncture or opening 102 in a vessel 100. More specifically, a wall of the vessel 100 is punctured with a needle, trocar, or other device 106 attached to a medical device 104. The needle 106 creates the opening 102 in the vessel and the needle 106 is often used to insert a guide wire into a lumen 112 of the vessel 100. Once the needle 106 is removed (typically leaving the guide wire in place), other medical devices can access the lumen 112 of the vessel 100 through the opening 102. Medical procedures, such as stenting procedures and the like, are often performed through the opening 102 in the vessel 100. As these procedures are performed, the necessary devices are often introduced into the patient's vascular or other system through the opening 102 in the vessel 100.

Figure 2:
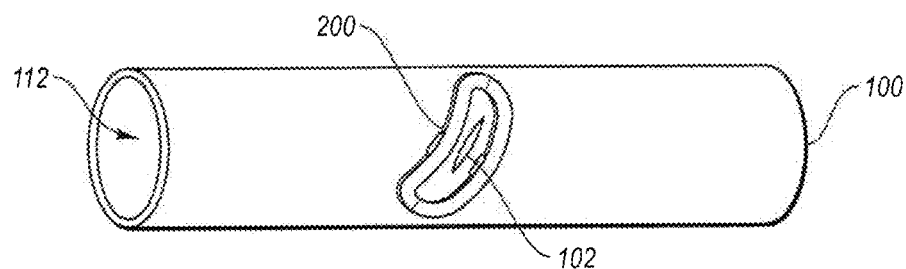
FIG. 2 shows an illustrative example of an access device that controls or manages access to a body lumen, such as a blood vessel, through the opening.

FIG. 2 shows an illustrative example of a clip 200 that controls or manages access to the vessel 100 or to the lumen 112 of the vessel 100 through the opening 102. The clip 200 can be placed or attached to the vessel 100 before or after the opening 102 is formed in the vessel 100. However, the clip 200 is typically placed before other medical devices (e.g., an introducer sheath) such that the clip 200 can minimize additional trauma (e.g., tearing) of the vessel 100 at the opening 102.

FIG. 2 shows the clip 200 anchored or secured to the vessel 100 around the opening 102. The clip 200 may be embedded in or fixed to the wall of the vessel 100 or have an engagement mechanism that can attach or affix to the wall of the vessel 100. The attachment or connection between the clip 200 and the vessel 100 can be temporary and the clip 200 can be removed or repositioned if necessary. However, the clip 200 can remain attached with the wall of the vessel 100 during the procedure or as long as necessary. In some instances, the clip 200 may be formed from biodegradable or biocompatible material and/or be left in place long-term.

FIG. 2 also illustrates that the clip 200 and may be shaped such that the opening 102 is closed or substantially closed when the clip 200 is initially deployed. During deployment, the clip 200 may be expanded slightly such that the clip 200 closes the opening 102 once the engagement mechanism engages the walls of the vessel 100. Because the clip 200 is expandable or deformable, the clip 200 can deform to accommodate other medical devices and enable access through the opening 102. However, a second closure mechanism, such as a suture, staple, medical clip, plug, or other closure mechanism, or combinations thereof may be used.

Figure 3:
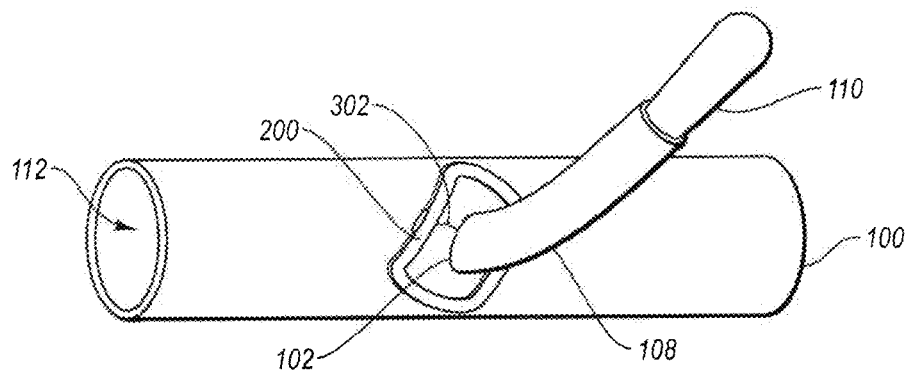
FIG. 3 shows an illustrative example of the access device of FIG. 2 in an expanded position to accommodate the introduction of a medical device through the opening in the body lumen.

FIG. 3 shows an illustrative example of the clip 200 in an expanded position to accommodate the introduction of a medical device 110 through the opening 102 in the vessel 100. FIG. 3 shows a medical device 110 being used to access the lumen 112 of the vessel 100. Often, the medical device 110 is introduced to the lumen 112 via an introducer sheath 108. When the introducer sheath 108 (or other device) is inserted through the opening 102, the clip 200 expands or deforms to accommodate the introducer sheath 108.

Because the introducer sheath 108 is typically larger than the needle 106 that initially formed the opening 102. The larger size of the introducer sheath 108 may cause the opening 102 to stretch or expand in order to accommodate the introducer sheath 108. The clip 200 may be able to control or at least limit the ultimate size of the opening 102. For example, the clip 200 may prevent or limit tearing of the opening 102 during a medical procedure or during portions of the medical procedure (e.g., introduction of the introducer sheath 108) and thus help reduce or minimize trauma at the opening 102.

The size of the clip 200 can vary. The clip 200 is typically selected according to the medical devices that are being used for a given procedure. The clip 200 should be selected such that when the clip 200 is fully expanded, the clip 200 can accommodate the necessary medical devices through the clip's interior. In some instances, the clip 200 may be larger than the medical devices such that the clip 200 does not itself impede the introduction and/or removal of the various medical devices. FIG. 3, for example, illustrates a space 302 between the clip 200 and the introducer sheath 108.

Once the procedure is finished and the introducer sheath 108 is removed, the clip 200 contracts or moves toward to its original shape as illustrated in FIG. 2. When the clip 200 returns toward its original or un-deformed state or when the clip 200 is actively closed, the opening 102 may be closed or substantially closed by the clip 200. In one embodiment, the clip 200 may serve as a vessel closure device in addition to providing vessel support during the procedure. In this case, the opening 102 may not require any additional procedures that would otherwise be performed to close the opening 102. However, a second closure mechanism, such as a suture, staple, medical clip, plug, or other closure mechanism, or combinations thereof may be used.

In one example, the clip 200 is deformed to open the clip as shown in FIG. 3. As a result, the clip 200 naturally closes. Alternatively, the clip may be deformed in order to close the clip 200. The clip 200 may be held closed, in one example, by a locking mechanism.

Figure 4A:
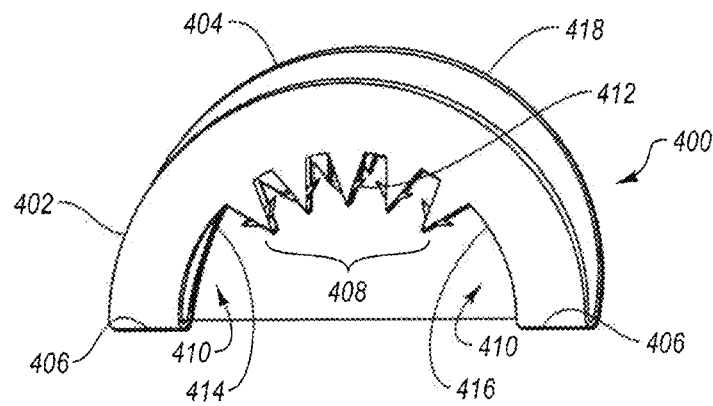
FIG. 4A shows an illustrative example of an access device in a first closed position.

FIG. 4A shows an illustrative embodiment of a clip 400, which is an example of the clip 200, in a closed position shown in a perspective view. As previously mentioned, the clip 400 can be deformed such that dimensions or shape of an interior 410 can be changed. Changing the dimensions of the interior 410 enables medical devices of different sizes to be accommodated in the interior 410 defined by the clip 400.

The clip 400 may be formed of any material that would bias the clip toward the closed position or may be formed such that the clip can self-bias in two different positions. For example, the material may have shape memory. The clip 400 is usually set in the closed position. As the clip 400 is expanded to an expanded position (e.g., to accommodate the introduction and/or removal of various medical devices), the clip 400 moves toward the closed position in the absence of an expanding force. The clip 400 may alternatively be deformable to achieve the closed position. In deforming the clip in this example, the clip may be moved towards a locking mechanism to keep the clip 400 in the closed position.

In FIG. 4A, the clip 400 is illustrated as having a body that includes a first portion 402 joined with a second portion 404. As shown, clip 400 may be at least partially folded at a fold 406. FIG. 4A illustrates that the portions 402 and 404 are curved and join at the fold 406. In one embodiment, the portions 402 and 404 are symmetrical, although the portions 402 and 404 can be non-symmetrical. The clip 400 can be deformed in multiple dimensions as well. For example, the clip 400 can be flattened. In addition or in the alternative, at least a part of the clip's body may twist or rotate. In addition, a curve 416 of the portions 402 and 406 may be shaped to accommodate a vessel, for instance. The curve 416 may be, by way of example only, circular, elliptical, or otherwise shaped. Deformation or expansion of the clip 400 may change a shape of the curve 416 as well. However, the curve 416 can be more flat or curved as well in either the closed or expanded positions.

The clip 400 may be shaped to accommodate specific tissue and to be used with specific openings, such as an opening in a vessel. For example, the clip 400 may be selected according to the body lumen being accessed. Larger clips may be used with larger vessels. In addition, the size of the medical devices may have an impact on the size of the clip selected because the medical devices are typically inserted through interior 410 defined by the portions 402 and 404 of the clip 400.

The clip 400 may include prongs 408 that extend inwardly from each of the first portion 402 and the second portion 404 into the interior 410 or in the general direction of the interior 410. During deployment, the clip 400 may be at least partially expanded and placed at the opening in the vessel such that the prongs 408 engage the tissue (e.g., vessel wall) around the opening. The clip 400 can then be released. As the clip 400 returns toward its set shape or closed position, the portions 402 and 404 pull the tissue around the opening in a manner that closes or at least reduces a size of the opening in the vessel. The prongs 408 can engage the tissue around the opening and tearing of the opening can be reduced during a procedure as the clip 400 can constrain the medical device used during the procedure. In addition, at least a portion of any force exerted by the medical devices on the vessel wall may at least partially be borne by the clip 400 rather than solely by the vessel wall. As a result, the vessel is less likely to tear during the medical procedure.

Figure 4B:
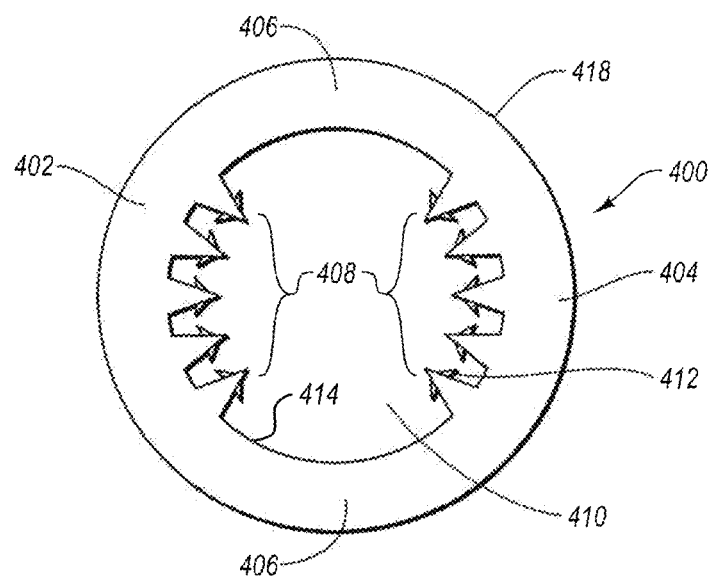
FIG. 4B shows an illustrative example of the clip in a second, expanded or open position.

FIG. 4B illustrates the clip 400 in an expanded or second position (the closed position may correspond to a first position). FIG. 4B illustrates that the prongs 408 extend from the portions 402 and 404 into an interior 410 defined by the portions 402 and 404. The prongs 408 are illustrated as being placed on or extending from an interior edge 414 of the clip 400. The prongs 408 can be placed anywhere on the interior edge 414 including at the fold 406. As described in more detail below, the prongs may also be configured to extend from the exterior edge 418 (as shown for example in FIG. 6B).

The arrangement of the prongs 408 can vary. For instance, the prongs 408 can be arranged in groups on the interior edge 414. FIG. 4B illustrates that the prongs 408 are arranged in two groups on opposite sides of the interior edge 414. However, the prongs 408 can be arranged in other groups and be placed symmetrically and or asymmetrically on the interior edge 414. The number of prongs 408 in each group can be the same or different. The configuration of the prongs 408 may be selected according to a size of the opening and/or to control trauma to the vessel. In addition, the prongs 408 can be substantially straight, have one or more curves along their length, have a varying width and/or thickness.

The prongs 408 can also vary according to shape. In some instances, the prongs 408 may have different shapes or lengths and may be oriented in different directions. Some of the prongs 408 may extend further into the interior 410 than other of the prongs 408. Some of the prongs 408 may be configured to completely pierce the tissue. For instance, some of the prongs 408 may be configured to engage a vessel wall by piercing the vessel wall. By engaging the vessel wall, the prongs 408 enable the clip 400 to close the opening in the vessel.

In another example, some of the prongs 408 may only partially pierce the vessel wall. The prongs 408 may have different widths and/or lengths. The prongs 408 may have different or the same thicknesses. In addition, deformation or expansion of the clip 400 can change the direction in which the prongs 408 are oriented. In other words, the prongs 408 may be flexible in order to accommodate changes in the orientation or position of the clip 400. Barbs 412 may also be located on at least some of the prongs 408. The barbs 412 are typically oriented to prevent the clip 400 from detaching from the vessel wall. The barbs 412 are positioned to allow insertion of the prongs 408 into the vessel walls while resisting extraction of the prongs 408 from the vessel's walls. In other examples, prongs 408 may be excluded and/or replaced by another engagement mechanism. In some examples, a single prong (or more) may be oriented in a non-planar configuration and may have barbs that extend in different directions.

Figure 4C:
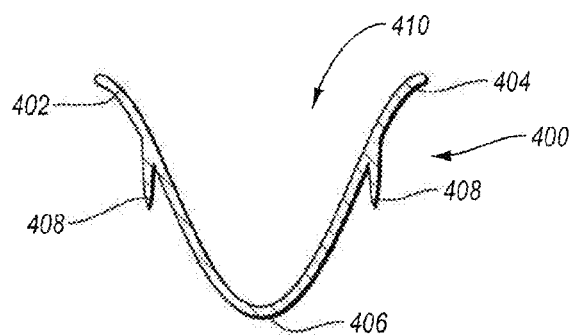
FIG. 4C shows a side view of the access device in a first, closed position.

FIG. 4C illustrates a side view of the clip 400 in the closed position. FIG. 4C illustrates that the prongs 408 can extend from the portions 402 and 404 in different ways. The prongs 408 may extend substantially straight or laterally from the portions 402 and/or 404. Alternatively, the prongs 408 may be angled relative to the portions 402, 404. In FIG. 4C, the prongs 408 are directed towards the interior 410 but are also are angled away from the interior 410 in the closed position. FIG. 4C illustrates that the prongs 408 may not extend straight from the edge 414 (shown in FIGS. 4A-4B), but may extend at an angle from the edge 414. The orientation of the prongs 408 may have an influence on how the clip 400 engages the tissue. The prongs 408 can be angled towards or away from the opening in the tissue. In addition, the prongs 408 may be curved. For instance, the prongs 408 may begin curving away from the interior 410 and then curve back towards the interior 410.

From a center of the clip, the body may be generally circular and have a radius of curvature. The radius of curvature can vary and be adapted to any potential deployment location.

Figure 4D:
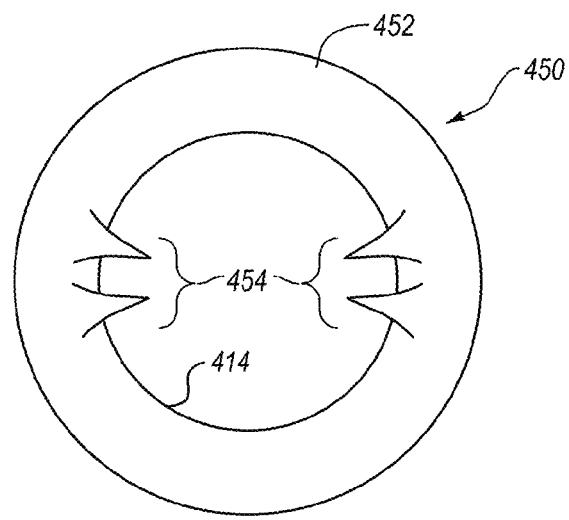
FIG. 4D illustrates an example of the access device where the prongs originate from a body of the clip rather than an internal or external edge of the clip.

FIG. 4D illustrates another example of a clip 450, which is an example of the clip 400. In the clip 450, prongs 454 originate from a body 452 of the clip 450 and not necessarily from the edge 414. The prongs 454 shown in FIG. 4D may have a gap between at least some of the prongs 454 and the body 452 of the clip 400. The prongs 454 can extend from a variety of locations and in a variety of configurations. The prongs 454, like other embodiments disclosed herein, may be directed towards a center of the clip 450 or more towards a side of the clip 450 or away from the body of the clip 450.

Figure 4E:
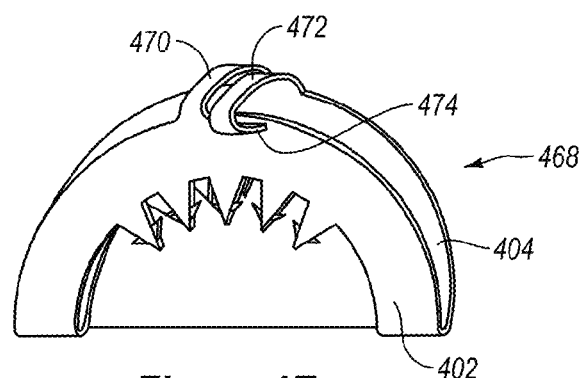
FIG. 4E illustrates the access device with a latch configured to hold the access device in a closed position.

FIG. 4E illustrates an example of the access device or clip 468 with a latch configuration. The latch configuration may include a first latch 470 and/or a second latch 472. A single latch may be used. The configuration of each latch is similar. In FIG. 4E, the latch 472 extends from a portion (e.g., an outer edge) of the portion 404. The latch 472 has a tip 474 that is configured to extend towards a center of the clip 468 in the closed position. In an open position, the latch 472 expends up when the body of the clip 468 is substantially flat. The latch 472 is flexible such that the latch 472 can be bent (and will return to its original shape from being bent) as necessary such that the outer edge of the portion 402 is held by the tip 474. The tip 474 may be rounded such that when the clip 468 is closed, latch 472 can snap into place once the portion 402 moves towards the portion 404 and is past the tip 474. A rounded tip 474 enables the edge of the portion 402 to lift the tip 474 until the outer edge passes the tip 474. At that point when the edge of the portion 402 passes the tip 474, the latch 472 returns to its original configuration and the clip 468 is held in a closed position. Because the portions 402 and 404 are biased towards an open position, lifting the tip allows the portions 402 and 404 to spread to the open position automatically. The latch 472 may have a rounded body that extends from an outer edge of one portion 404 and curves toward the other portion 402. The latch 470 may be similarly configured.

Figure 5A:
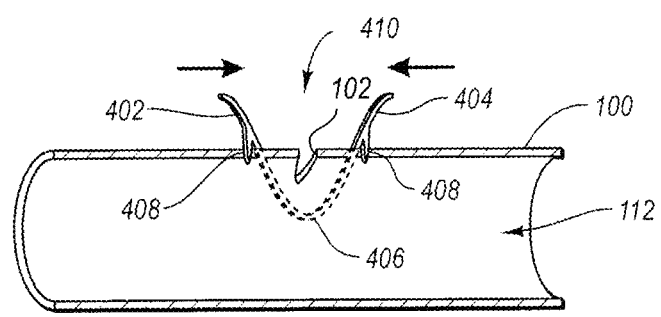
FIG. 5A shows an example of the access device in a first, deployed position in tissue.
Figure 5B:
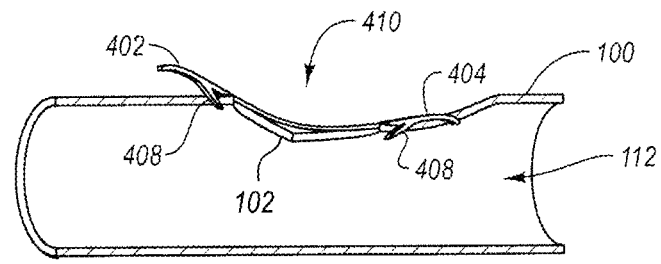
FIG. 5B shows an example of the clip in a second, expanded position to accommodate introduction of a medical device.

FIGS. 5A and 5B illustrate the clip 400 deployed in a body lumen, such as a blood vessel 100. FIG. 5A illustrates the clip 400 in the closed position. In the closed position, the prongs 408 at least partially engage the walls of the vessel 100. The opening 102 in the vessel 100 can be held at least partially closed by the clip 400. As previously stated, the clip 400 may be partially expanded when attached to the vessel 100. This enables the prongs 408 to engage the vessel wall and pull the wall around the opening together. Alternatively, the clip 400 can be pressed such that the prongs 408 engage the vessel wall. Alternatively, the clip 400 can engage the vessel 100 without being partially expanded. As the clip 400 is expanded, the prongs 408 turn towards the opening 102 in the vessel 100. This enables the clip 400 to more firmly engage the vessel 100 in an expanded position.

FIG. 5B illustrates the clip 400 in the expanded position. To reach the expanded position, the portions 402 and 404 are generally pushed away from each other. The direction in which the portions 402 and 404 are pushed can depend on the relative orientation of the portions 402 and 404. In one example, both the open and closed positions may be in substantially in the same plane. Alternatively, the clip 400 may deform at least at the fold 406 to enlarge the interior 410. As a result, pushing the portions 402 and 404 away from each other tends to unfold the body of the clip. In the expanded position, the prongs 408 continue to hold the vessel walls and allow the introduction of medical devices. As indicated above, the prongs 408 turn inward towards the opening during expansion of the clip 400. The clip 400 can be expanded merely by the introduction of a medical device. In other words, the medical device itself may serve as an expander for the clip 400. The clip 400 does not significantly impede the introduction of the medical device. At the same time, the clip 400 can prevent or reduce tearing in the opening.

Further, the prongs 408 are typically positioned such that they do not impede withdrawal of any medical devices. This can be achieved by controlling a length of the prongs 408, selecting a placement of the prongs 408 on the interior and/or exterior edges 414 and 418 of the clip 400, the orientation of the prongs (towards the center of the clip, away from the clip), and the like. For instance, the portions 402 and 404 may each have two prongs that are laterally spaced or placed closer to the fold 406. Placing the prongs near the fold 406 leaves the interior 410 of the clip 400 substantially free of prongs to enable the introduction of medical devices while still allowing the clip 400 to engage the vessel and protect the vessel from future trauma.

Figure 6A:
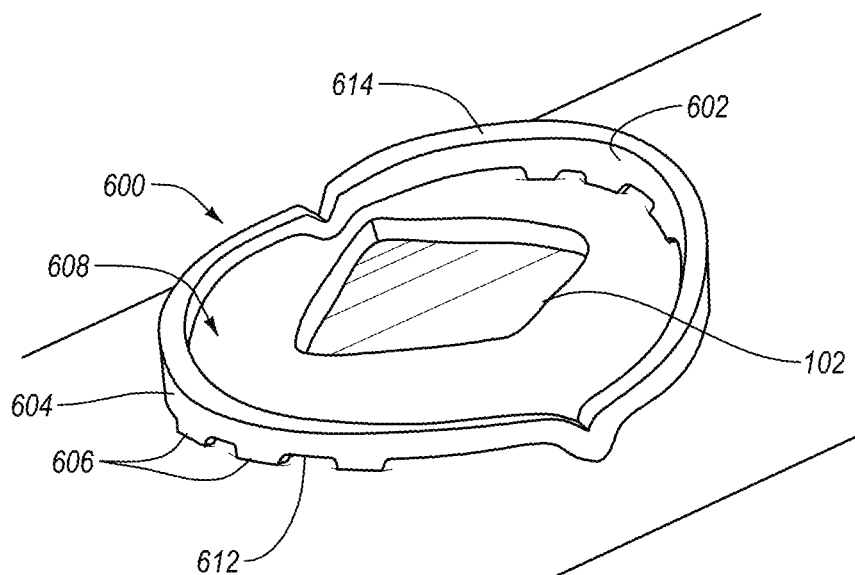
FIG. 6A shows another illustrative example of an access device or clip with prongs on an outer edge of the access device and in an expanded or open position.
Figure 6B:
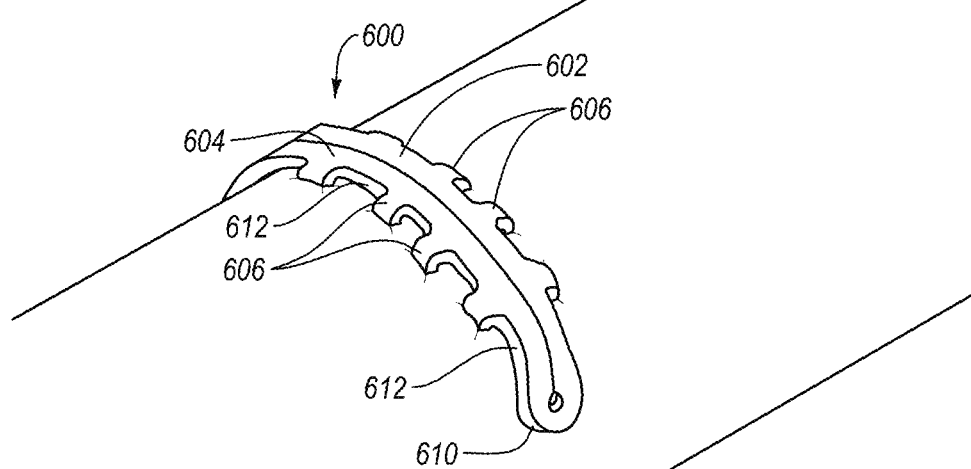
FIG. 6B shows the access device of FIG. 6A in a contracted or closed position.

FIG. 6A shows an illustrative example of another embodiment of a clip 600 in an open or expanded position. The clip 600 may be an example of other clips or access management devices discussed herein. FIG. 6A shows the clip in an open or expanded position. FIG. 6B shows the clip 600 in a closed position. FIGS. 6A and 6B illustrate the clip 600 deployed at an opening 102 in a vessel 100. The clip 600 includes a portion 602 and a portion 604 that may be similar to the portions 402 and 404 described herein. The clip 600 also includes prongs 606, in this example, that are located on or extend from a bottom or an outer edge 612 of the clip 600 and which are embedded in a wall of the vessel 100. More specifically, the prongs 606 may appear to extend from a bottom of the clip 600 in the open position illustrated in FIG. 6A. An orientation of the edge 612 changes as the clip 600 moves between the open and closed positions. The prongs 606 on the portion 602, in the closed position, may be angled toward the prongs 606 on the portion 604. Alternatively, the prongs may be angled away from the opening 102.

During deployment of the clip 600, the clip 600 may be expanded, although expansion during deployment is not required. In deploying the clip 600, the prongs 606 engage the walls of the vessel 100 and the clip is in closed position as shown in FIG. 6B. In fact, the clip 600 can be deployed in the closed position. In one example the vessel is split or opened after the clip 600 (or other clip illustrated herein) is deployed in the closed position. Thus, the vessel can be split or opened to form the opening 102 when the clip is in the closed position as shown in FIG. 6B in one example. The clip 600 can keep the opening 102 substantially closed even after the opening 102 is formed. The clip 600 can then be expanded to the open position as illustrated in FIG. 6A. Insertion of a device, by way of example, may open or expand the clip 600 to the open position illustrated in FIG. 6A. After the device is withdrawn or when the clip 600 is released, the portions 602 and 604 contract towards each other to generally close the opening 102 by bringing the walls of the vessel together as the portions 602 and 604 move towards each other to close the opening 102. In this example, the prongs 606 on the portion 602 are embedded on one side of the opening 102 and the prongs 606 on the portion 604 are embedded on a different side of the opening 102. As a result, opening and closing the clip 600 can open and close the opening 102. This enables access to the lumen of the vessel 100 to be controlled. For example, the clip 600 can be expanded to allow the introduction of other medical devices through the interior area 608 defined by the clip 600 when in the open position. And the clip 600 can be closed as necessary. The clip 600 can be opened manually without a device being inserted or closed manually. Alternatively, insertion of a device through the clip 600 may open the clip 600 and withdrawal of the device may automatically result in the clip 600 contracting to close the opening 102.

The prongs 606 are oriented to engage the wall of the vessel 100 around the opening 102. The prongs 606 on the portion 602 may be angled towards the prongs 606 on the portion 604 of the clip 600.

In one example of the clip 600, the clip 600 may have a memory such that the unbiased position of the clip 600 is closed, as illustrated in FIG. 6B. However, the clip 600 may alternatively be configured to be bi-modal such that the clip 600 can remain closed without any external bias and the clip 600 can also remain open without any external bias. In this example, the portion 602 and/or the portion 604 may flex in a manner that causes the clip 600 to remain in the open position.

The portions 602 and/or 604 may be configured such that as the clip 600 moves from one position (e.g., closed) to another position (e.g., open), the portions may begin to bend or deform. At a certain point in the deformation, the portions snap or become biased towards the other position. Thus, the clip 600 becomes bi-modal and can remain stable in either the open or closed position.

Figure 7A:
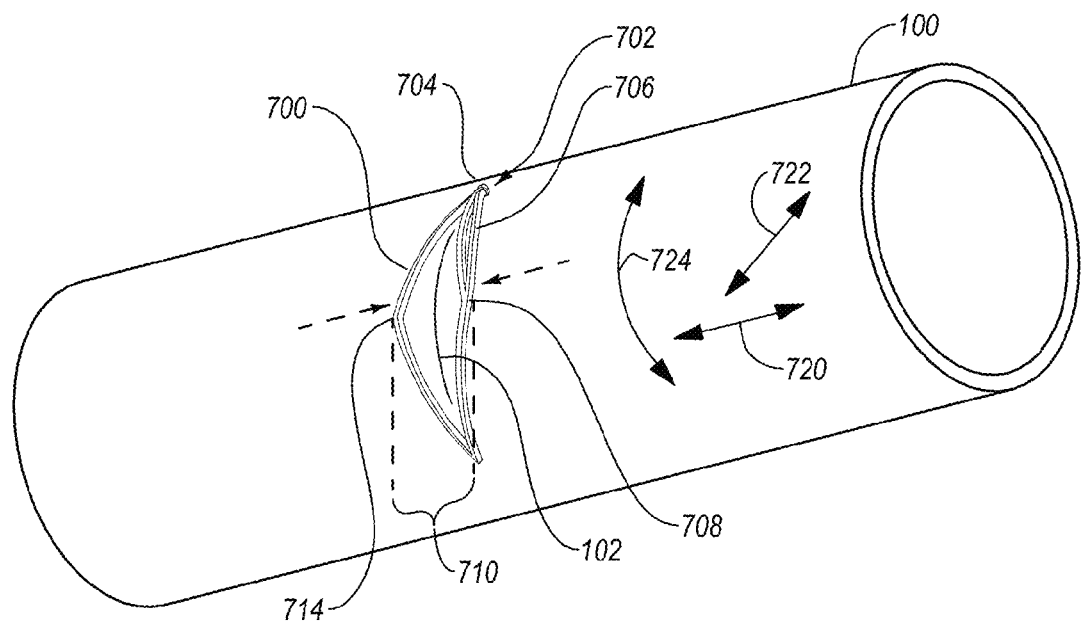
FIG. 7A illustrates an access device or bi-modal clip biased in a closed position.
Figure 7B:
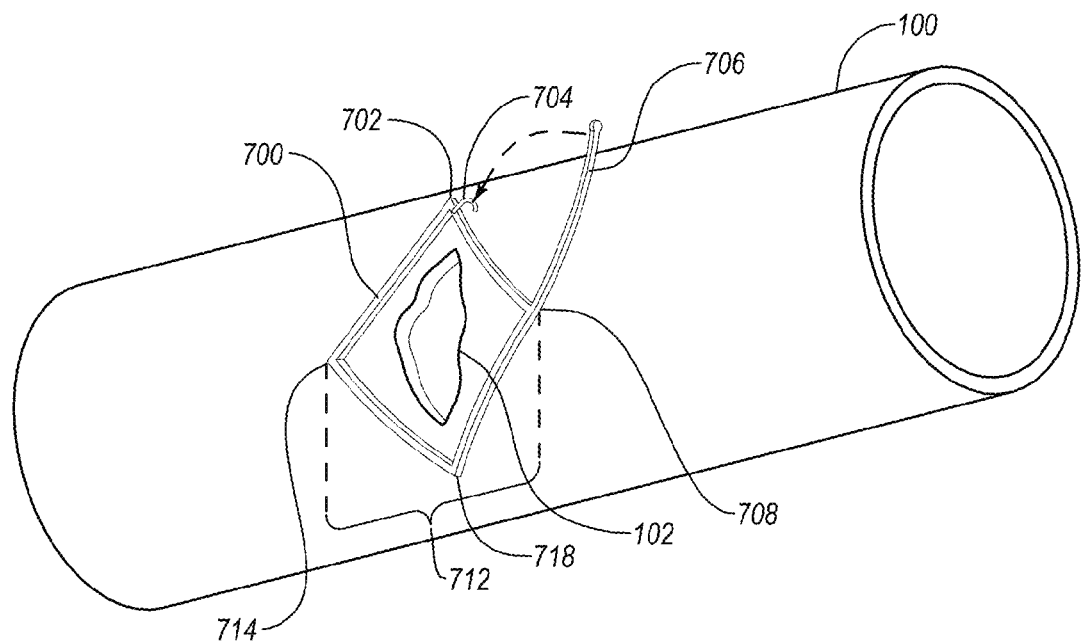
FIG. 7B illustrates the bi-modal clip in FIG. 7A in an open and unbiased position.

FIGS. 7A-7B illustrate another embodiment of an access device or clip having a body 700 in closed position and an open position. FIG. 7A illustrates the clip 700 in a closed position and FIG. 7B illustrates the clip in an open position. The clip 700 may be configured to have a diamond, square, or rectangular orientation or shape. The clip 700, however, may also have a circular or ellipsoidal shape or orientation or other shape.

The clip 700 may include a bar 706 that cooperates with a latch 704 to bias the clip 700 in a closed position as shown in FIG. 7A. The bar 706 connects with or extends from the body of the clip 700, at a corner 708 for example or from another location on the body of the clip 700. The bar 706 may be an integral part of the body of the clip 700.

The bar 706 and the clip 700 are configured such that movement of the bar 706 towards the latch 704 applies a bias to the body of the clip 700 and causes the corners 708 and 714, or more generally, the sides of the clip to move towards each other. The movement may occur in more than one dimension. For example, as the sides of the clip move towards each other, the ends 718 may move in another direction (e.g., up or down or perpendicularly to the movement of the sides of the clip 700. The portions of the clip can thus be reoriented in a direction along a longitudinal axis of the vessel, in a circumferential direction around the vessel 100, transverse to the longitudinal axis of the vessel 100, or any combination thereof.

Movement of the bar 706 can flex the clip 700 such that the sides or corners 708 and 714 move in the direction 720 and/or the direction 722. Further, the clip 700 may have a curved shape 724. Because the clip 700 may include prongs in an example (similar to prongs described herein and located on an exterior side and/or an interior side or edge of the clip), the opening 102 is closed when the clip 700 is moved to the closed position. As a result, the clip 700 in the open position shown in FIG. 7B may have a planar shape and closure of the clip 700 may provide a curvature 724 (see FIG. 7A) to the body as the sides are drawn in towards each other in one or more directions (e.g., directions 720 and 722).

The bar 706 may be operative to bias the clip 700 in a closed position. The bar 706 can be operated (moved) to transition or bias the clip 700 to the closed position. For example, pushing on the bar 706 in a particular direction can apply a biasing force that moves the clip 700 to the closed position. When the biasing force is removed, the clip 700 returns to its original shape. In the closed position, a width 710 of the clip 700 is smaller than a width 712 in an open position as shown in FIG. 7B.

The clip 700 shown in FIG. 7B may have a planar or substantially planar shape such that the clip 700 can lie flat against a surface of the vessel 100. Alternatively, the clip in the closed position may have some curvature and the surface of the vessel may adapt to the shape of the clip 700. When the bar 706 is moved inwards, the planar shape or curved shape may deform to become more curved as illustrated in FIG. 7A.

The opening 102, for example, may be pinched closed by a change in the shape of the clip 700 when moving to the closed position. The bar 706 can then removably engage with the latch 704 to hold the clip in the closed position, which can close the opening 102 in the vessel 100. The latch 704 may be a curved hook, or other structure configured to at least temporarily hold the bar 706. Because the clip 700 is anchored to the vessel 100 as disclosed herein, the latch 704 can cooperate with the bar 706 to keep the clip 700 in the closed position. When the bar 706 is unlatched or uncoupled or disconnected from the latch 704, the clip 700 returns to an unbiased or open position shown in FIG. 7B.

In another example, the clip 700 may not include the bar 706 or the latch 704. In this example, the clip is configured to have an inflection point that can be used to move the clip 700 between two positions (e.g., the open and closed positions). The sides of the clip 700 may be configured such that when the ends 702 and 718 are bent, the clip 700 passes the inflection point and snaps to the open position.

The clip 700 can be adjusted from the closed position to the open position by pushing in one direction on the ends 702 and 718 while the middle of the clip 700 is biased or pushed in the other direction. Similarly, adjusting the clip 700 from the open position to the closed position can be achieved by pushing on the ends 702 and 718 while a force is applied to the middle of the clip 700. The direction of the forces depends on the current position of the clip. In this example, once the clip (starting from one position) is pushed or forced past an inflection point, the clip is configured to snap to the other position.

Figure 8A:
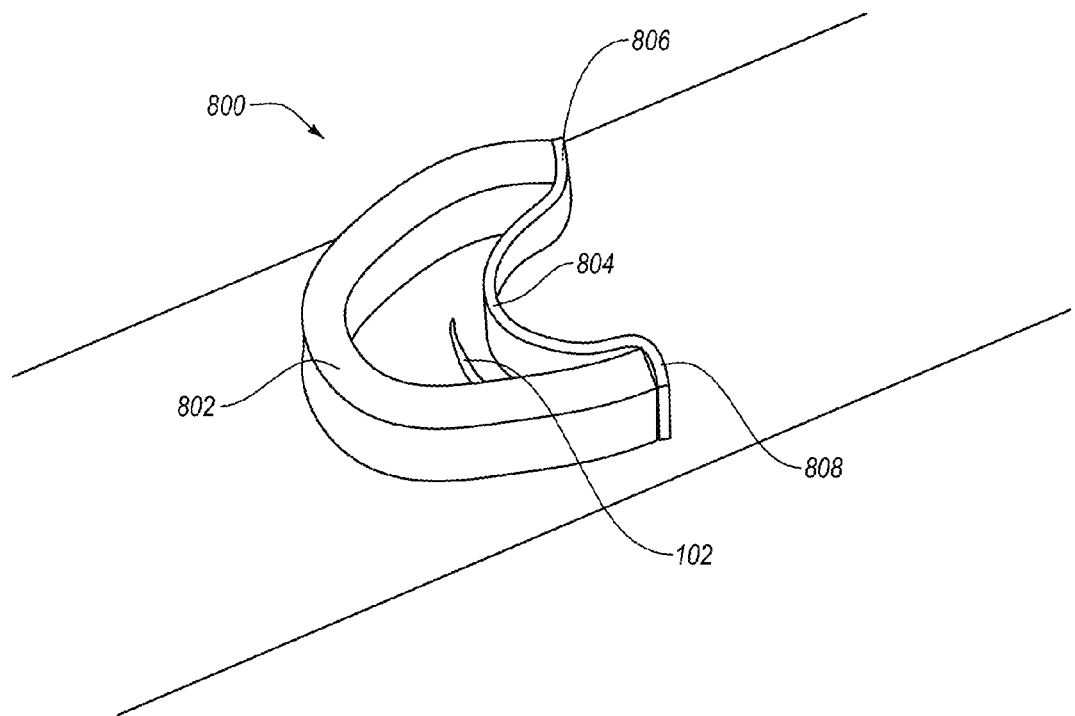
FIG. 8A illustrates another example of a bi-modal clip configured to control access to tissue in a closed position.
Figure 8B:
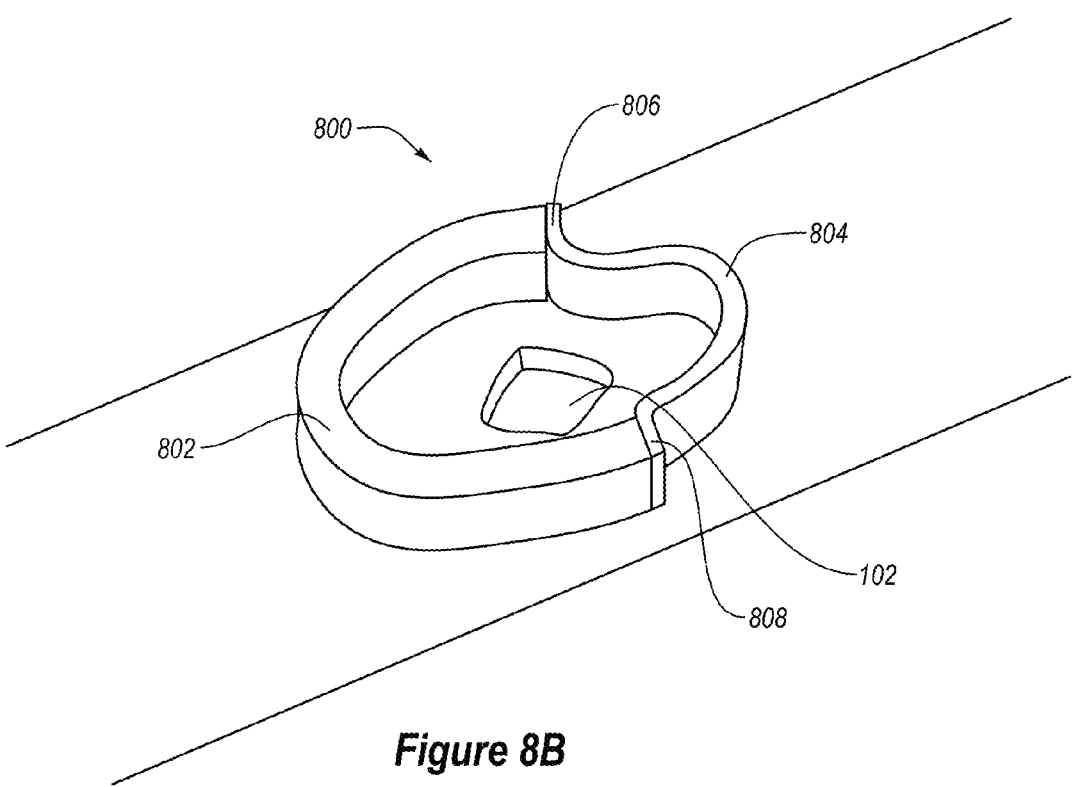
FIG. 8B illustrates the bi-modal clip of FIG. 8A tissue in an open position.

FIGS. 8A-8B illustrate another example of a bi-modal clip. FIG. 8A illustrates a clip 800 in a closed position and FIG. 8B illustrates the clip 800 in an open position. A clip 800 includes a body having a first portion 802 and a second portion 804. The first portion 802 is attached to the second portion at attachment points 806 and 808. The portion 802 and the portion 804 can, however, be formed as a single integral body.

In one example, the portion 802 may have a thicker and/or stiffer body and the portion 804. As a result, the portion 804 can flex between the closed position shown in FIG. 8A to the open position shown in FIG. 8B. The portion 804 can bend towards the portion 802 to keep the opening 102 substantially closed.

More specifically, the portion 804 is configured to have a length that is longer than a distance between ends 806 and 808. As a result, the portion 804 can be bent in towards the portion 802 to close the opening 102. The portion 804 can then be pushed away from the portion 802. During this transition to the open position, the portion 804 may deform in order to accommodate the transition. At a certain point of the transition, spring of the portion 804 pushes the portion 804 away from the opening 102 and/or the portion 802, which opens the opening.

The portion 804 may not plastically deform. However, the portion 804 can be biased in the closed position shown in FIG. 8A and biased in the open position shown in FIG. 8B. No external force (e.g., the insertion of a medical device) is required to keep the clip 800 in the open position or the closed position. In one example, the portion 804 is less stiff than the portion 802. The flexibility of the portion 804 enables it to be moved from the closed position to the open position. The portion 804 has a length that is longer than a distance between ends of the portion 802 to which the portion 804 is attached. As a result, the portion 802 is curved outwardly in the open position and inwardly in the closed position. The curve in the portion 802, whether inwardly or outwardly oriented, prevents the portion 802 from transitioning from the closed position to the open position or vice versa without an external force.

Both portions 802 and 804 may have prongs that embed in the vessel. As a result, opening and closing the clip 800 opens and closes the opening 102 since the clip 800 is attached to the vessel walls surrounding the opening.

In one example, the portion 802 has a body shaped to surround (e.g., "U" shaped) the opening 102 at least partially. The portion 802, as previously stated, may be less subject to deforming to enable the portion 804 to snap between the open and close positions. The portions 802 and 804 may also have substantially the same length such that, when the clip 800 is in the closed position, the portions 802 and 804 are close and may be in contact with each other. In this manner, the opening 102 can be closed or substantially closed by the clip 800. The portions may, in some embodiments, have different lengths.

The bi-modal clip illustrated in FIGS. 8A-8B illustrated can maintain more than one position. The clip 800 can control access to tissue by opening the opening 102 when desired and by closing the opening 102 when desired. In one example, the portions 802 and 804 stay in substantially the same planar orientation when transitioning from one position to another. Even if the body of the clip 800 is curved to accommodate a surface of the vessel, the movement of the portion 804 relative to the portion 802 occurs laterally in one embodiment. However, the bimodality of the clip 800 can occur in more than one direction or dimension.

The portions 802 and 804 (as well as portions of other clips discussed herein) may be formed of the same or of different materials Example materials include, but are not limited to, stainless steel, titanium, nitinol, elgiloy or other suitable materials, or combinations thereof some of which may have a memory effect. More generally, these materials may be included in other embodiments disclosed herein.

Figure 9A:
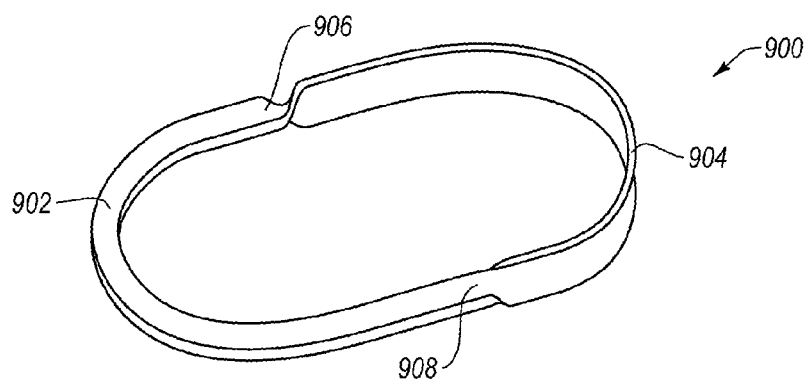
FIG. 9A illustrates a perspective view of another bimodal clip.
Figure 9B:
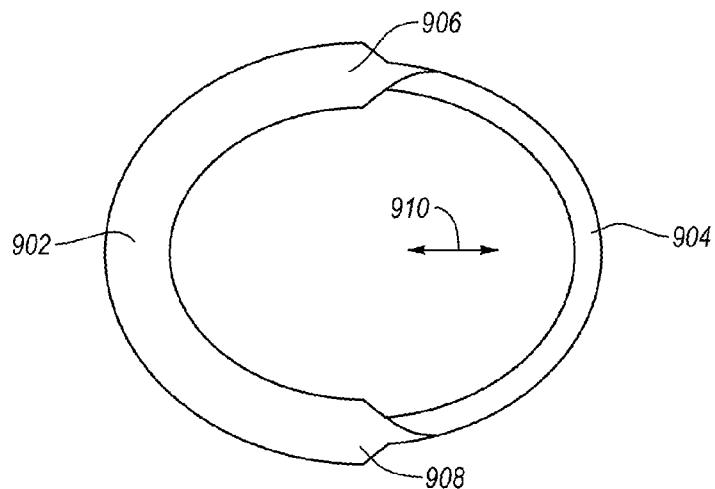
FIG. 9B illustrates top view of the bimodal clip shown in FIG. 9A in a first position.
Figure 9C:
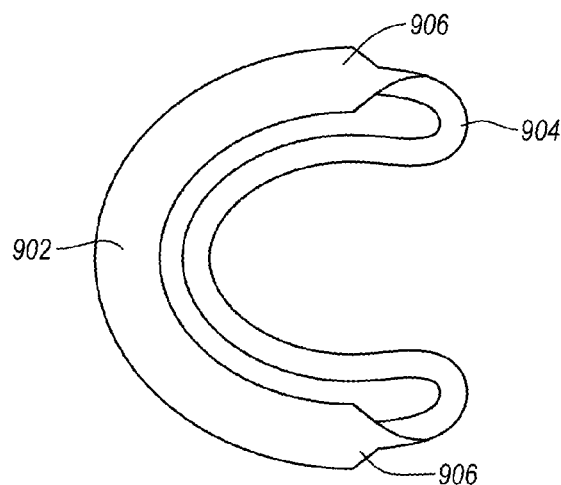
FIG. 9C illustrates a top view of the bimodal clip shown in FIG. 9A in a second position.

FIGS. 9A-9C illustrate another example of a bi-modal clip. A clip 900 includes a portion 902 and a portion 904. The portions 902 and 904 may each have approximately half of the clip's body, but other proportions may be possible. The clip 900 has a body that is formed from a single integral loop. The loop 902 is separated from the portion 904 at locations 906 and 908. The body of the clip 900 is twisted such that the portion 904 is oriented at an angle with respect to the portion 902.

In one example, a thickness and a width of the portion 902 may be substantially the same as a thickness and a width of the portion 904. However, the portion 904 is twisted or rotated with respect to the portion 902.

FIG. 9B illustrates a top view of the clip 900 in an open position and FIG. 9C illustrates the clip 90 is a closed position. The clip 900 may engage a vessel or tissue surrounding an opening as described herein. Thus, both the portion 902 and the portion 904 may have an engagement mechanism, such as prongs, that are configured to engage with the tissue to keep the clip 900 removably attached to the vessel or tissue.

Because the portion 904 is rotated or twisted with respect to the portion 902, the portion 904 can be moved between open position illustrated in FIG. 9B and the closed position illustrated in FIG. 9C. The portion 904 of the clip 900 can move in directions shown by the arrow 910. Advantageously, the clip 900 is configured such that the clip 900 can self-maintain the open position and the closed position.

More specifically, a spring force of the portion 904 keeps the clip 900 in the open position. The portion 904, because it is twisted, is flexible in the directions of the arrow 910. The portion 902, in contrast, is much less flexible in the directions of the arrow 910. However, as the portion 904 moves between the open position and the closed position, ends of the portion 902 may flex outwardly to assist the portion 904 in transitioning from the open position to the closed position and vice versa.

When the potion 904 is pushed towards the portion 902, the middle bends inwardly. At a certain point, the portion 904 reaches a transition point and snaps to the closed position shown in FIG. 9C. The ends of the portion 902 may exert an inward force at the locations 906 and 908 to keep the clip in the closed position.

When the portions 902 and 904 are connected or engaged with tissue and an opening is located inside the clip 900, moving the clip 900 as described herein manage access to the tissue by opening and/or closing the opening in the tissue. The clip 900 may exert pressure on the opening such that the opening can be held closed and no further closure mechanism (e.g., sutures or a closure element) is needed to permanently close the opening.

FIG. 9A illustrates that the locations 906 and 908 are twisted. The material can be formed in this position or heat set in this position. The clip 900 may be formed of Nitinol or other material that is elastically deformable.

Together, the portions 902 and 904 are circular in shape or elliptical in shape, although other shapes are possible. In one example, the portion 902 is generally "U" shaped with sufficient radius to accommodate and allow the portion 904 to move between the positions illustrated in FIGS. 9B and 9C. In this example, the width of the portion 902 is oriented in the same direction as the thickness of the portion 904. The difference in dimension helps keep the clip 900 oriented. In one example, this orientation ensures that the portion 904 can flex relative to the portion 902 while the portion 902 remains substantially stationary (even though it may move in a direction orthogonal to the arrow 910 when flexing or moving between the open and closed position.

In one example, the portions may be similarly configured and have similar stiffness. However, the orientation of the portion 902 to the portion 904 enables the portion 904 to be more flexible compared to the portion 902. Thus, the portion 904 can be used bi-modally to control access to tissue.

The clips 800 and 900, like other embodiments disclosed herein, may also include prongs extending from a body or from an edge of the body as appropriate such that the clip 800 and 900 can be attached to tissue. In some examples, the prongs of one portion (e.g., the portion 902) may extend from a body while the prongs of another portion (e.g., portion 904) of the clip 900 may extend from an edge of the body.

Figure 10A:
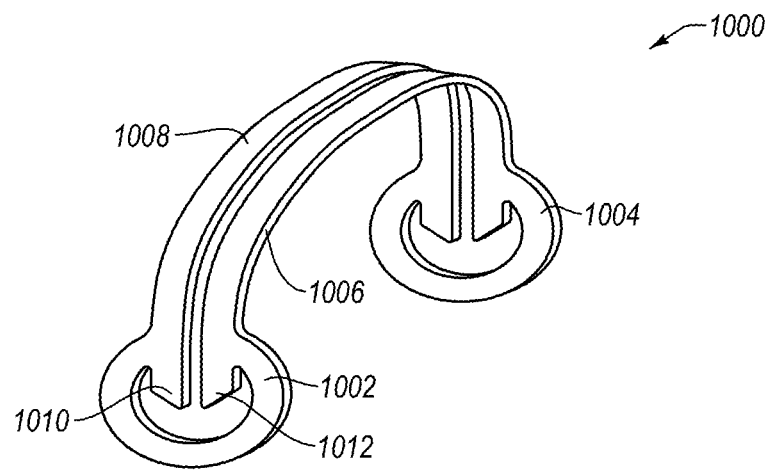
FIG. 10A illustrates a perspective view of another example of a bimodal clip.

FIG. 10A illustrates a perspective view of another example of a bi-modal clip. A clip 1000 include a portion 1006 and a portion 1008 ends 1010 and 1012 are connected by a connector 1002, which may be circular, elliptical or another shape. The other ends of the portions 1006 and 1008 are similarly connected. The connector 1002 connects to the portions 1006 and 1008 at a location above the ends 1010 and 1012 such that the ends 1010 and 1012 extend into a middle portion of the connector 1002.

The connector 1002 is configured to allow the portions 1006 and 1008 to be moved away from each other and towards each other. The connector 1002 ensures that the portions are automatically kept in either the open position or the closed position. The portions 1006 and 1008 may also have prongs extending therefrom in order to engage tissue. As described herein with respect to other examples of the clip, the clip 1000 can thus be used to manage access to tissue and keep an opening in the tissue either open or closed.

Figure 10B:
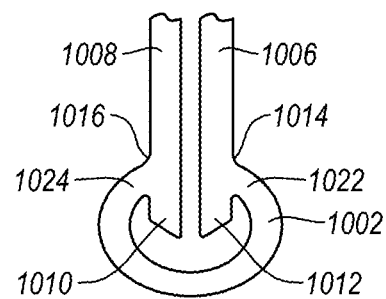
FIG. 10B illustrates a side view of the bimodal clip of FIG. 10A in a first position.

FIG. 10B illustrates the clip 1000 in the closed position and illustrates the positions of the portions 1006 and 1008 relative to the connector 1002. In one example, the ends 1022 and 1024 of the connector 1002 can push against or near the ends 1010 and 1012. Because the ends 1010 and 1012 extend into a middle portion of the connector 1002, the portions 1006 and 1008 cannot be inadvertently separated since separation causes the ends 1010 and 1012 to push against each other.

Figure 10C:
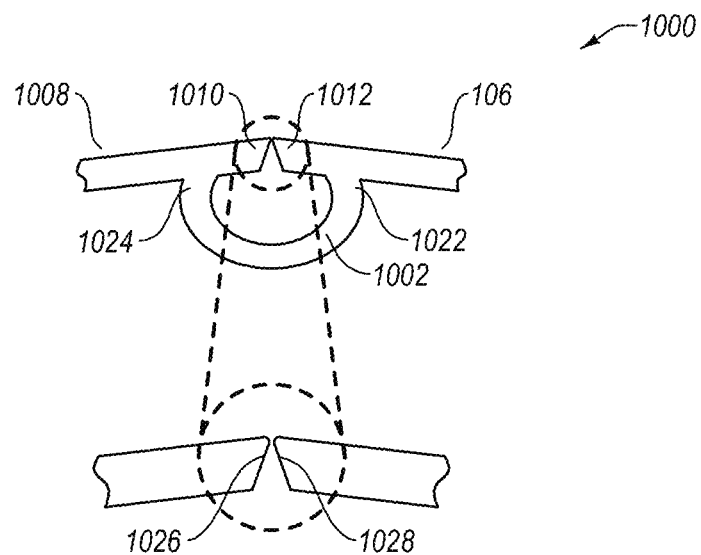
FIG. 10C illustrates the side view of the bimodal of FIG. 10A in the second position.

FIG. 10C illustrates the clip 1000 in the open position. In this example, the portions 1006 and 1008 are pushed away from each other. The ends 1010 and 1012 may be bent substantially flat or such that the ends 1010 and 1012 exert a force to keep the portions 1006 and 1008 away from each other. In the open position, the connector 1002 is expanded and may exert a force pushing the ends 1010 and 1012 towards each other. The ends 1010 and 1012, combined with the force exerted by the connector 1002 keep the clip 1000 in an open position. The ends 1010 and 1012 may include, respectively, flat portions 1026 and 1028 that are configured to abut against each other at least partially in the open position. By forming flat portions (or angled portions), the ends 1010 and 1012 provide a more stable surface and enable the clip to open to a particular orientation. In other words, as the clip moves to the open positions, the flat portions 1026 and 1028 may eventually abut against each other and allows the portions 1006 and 1008 to push against a flat surface, which can help the clip maintain the open position easier than if the ends are curved. The flat portions 1026 and 1028 may be located at different locations on the ends 1010 and 1012 (even though the relative placement may be the same in some examples) and may be placed on the ends 1010 and 1012 to cause the portions 1006 and 1008 to form an angle less than, equal to, or greater than 180 degrees in the open position (FIG. 10C illustrates that the portions 1008 and 1006 form an angle of about 180 degrees). In some examples, the open position is maintained without flat portions.

Figure 10D:
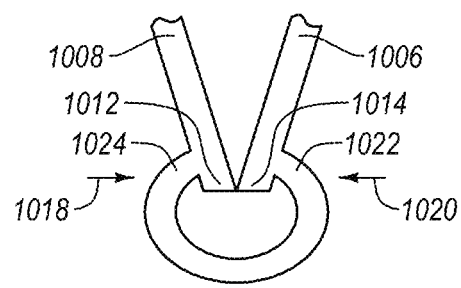
FIG. 10D illustrates the side view of the bimodal clip of FIG. 10A transitioning from the first position to a second position or vice versa.

FIG. 10D illustrates the clip transitioning from the open position to the closed position or vice versa. When the portions 1006 and 1008 are separated, for example, by a user, a resistive force is encountered by the ends 1010 and 1012 pushing against each other. As the portions 1006 and 1008 continued to be pushed apart, the connector 1002 begins to open to allow the ends 1010 and 1012 and more particularly the portions 1006 and 1008 to be separated. At a particular point, the clip 1000 snaps to the open position as the ends 1010 and 1012 reach a point where the connector 1002 can begin to close. Thus, the connector 1002 continues to push the portions 1006 and 1008 apart, but further separation is substantially prevented by the tissue in which the clip 1000 is engaged. The ends 1010 and 1012 may also have various geometries to hold the clip in the open position. For example, the ends 1010 and 1012 may have a flat portion or an angled portion that are configured to abut against each other when the clip is opened. This enables the clip itself to bear most of the force rather than the tissue. As a result, the force on the tissue is reduced or minimized, which reduces or minimizes trauma to the tissue.

Similarly, when the clip 1000 transitions from the open position to the closed position, the portions 1006 and 1008 can be lifted or moved towards each other. A resistive force is again encountered as the movement of the portions 1006 and 1008 towards each other cause the connector 1002 to expand. At a certain point when the ends 1010 and 1012 are in a certain position moving toward the middle portion of the connector 1012, the resistive force is overcome and the ring 1002 can close the clip 1000.

The connector 1002 of the clip 1000 is configured to allow the ends 1010 and 1012 to be arranged in a manner that allows the clip to stay in an open position. The connector 1002 may have a generally circular or elliptical shape that is open where the connector 1002 attaches to the ends 1010 and 1012. In this example, the ends 1010 and 1012 extend into a middle portion of the connector 1002. When the clip 1000 is opened, the ends 1010 and 1012 interfere or press against each other in the middle portion of the connector 1002. This causes the connector 1002 to expand. At a certain point, the ends 1010 and 1012 reach a position where the clip is effectively pushed to the open position as the ends 1010 and 1012 push against each other. When the ends 1010 and 1012 have a flat portion, these flat portions then abut against each other and provide stability to the clip and may keep the clip in a particular orientation.

FIGS. 10A-10D thus illustrate that the clip 1000 is a bi-modal clip that can be moved to either an open or closed position. The clip 1000 is configured such that the ends 1010 and 1012 of the portions 1006 and 1008 cooperate to bias the clip 1000 bi-modally to be held, without any other bias, in the open position or in the closed position.

In one example, the connector 1002 is an integral part of the portions 1006 and 1008. The clip 1000 may be formed of any suitable material, including memory material. Even if the bi-modal clip is formed of a memory material, the ends 1010 and 1012 may cooperate with the connector 1002 to keep the clip 1000 in a given position due to the biasing forces described herein.

Embodiments relate to clips configured to exhibit stability in two positions (e.g., an open or expanded position and a closed or unexpanded position). This bi-modality enables the clip to hold an opening closed or open according to need. As illustrated and discussed herein, bi-modal clips can be achieved using different configurations. Bi-modal clips can self-maintain in open or closed positions. At least some embodiments of the clips disclosed herein can be stable and maintain an open or closed position without an external force.

The bi-modality of clips is exemplarily illustrated when transitioning from one position to another. Because the clip can maintain either position, a force is typically applied to transition to another position. At a certain point of the transition, the shape of the clip causes the forces holding the state stably to switch to the other position. The inflection point is the point where the forces acting on the clip change to move the clip to the other position.

Some embodiments of the clips (e.g., the clip 468 in FIG. 4E and the clip 700 in FIGS. 7A-7B) may include a latch or a combination of a bar and a latch. The latches used in these examples can exhibit a snap action, a frictional or mechanical interaction that enables the clips to be held in either a closed or an open position. For example, one portion of the clip may include a small protrusion that frictionally fits in a corresponding opening formed in the other portion of the clip. The frictional fit may keep the clip in the closed position.

In some examples, the natural or unstressed position of the clips disclosed herein may be somewhere between a closed position and an open or a fully open position. As a result, some latches can be configured to hold the clip in the open and/or the closed position. Further, the clips can be deployed in various positions and can optimize tissue access control.

In one embodiment, a clip or clips of the present invention can include a material made from any of a variety of known suitable materials, such as a shape memory material (SMM). SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) including metal alloys, or shape memory plastics (SMP) including polymers.

The main types of SMAs are as follows: copper-zinc-aluminum; copper-aluminum-nickel; nickel-titanium (NiTi) alloys known as nitinol; and cobalt-chromium-nickel alloys or cobalt-chromium-nickel-molybdenum alloys known as elgiloy alloys.

A shape memory plastic (SMP) can be fashioned into a clip in accordance with the present invention. When an SMP encounters a temperature above the lowest melting point of the individual polymers, the blend makes a transition to a rubbery state. The elastic modulus can change more than two orders of magnitude across the transition temperature (Ttr). As such, an SMP can be formed into a desired shape of a clip by heating the clip above the Ttr, fixing the SMP into the new shape, and cooling the material below Ttr. The SMP can then be arranged into a temporary shape by force, and then resume the memory shape once the force has been removed. Examples of SMPs include, but are not limited to, biodegradable polymers, such as oligo($\epsilon$-caprolactone)diol, oligo(p-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present disclosure.

In one embodiment, the clip can include a variety of suitable deformable alloy metal materials, including stainless steel, silver, platinum, titanium, tantalum, palladium, cobalt-chromium alloys or other known biocompatible alloy metal materials.

In one embodiment, the clip can include a suitable biocompatible polymer in addition to or in place of a suitable metal. The clip can include biodegradable or bioabsorbable materials, which can be elastically, plastically, or otherwise deformable or capable of being set in the deployed configuration.

Moreover, the clip can include a radiopaque material to increase visibility during placement. Optionally, the radiopaque material can be a layer or coating any portion of the clip. The radiopaque materials can be platinum, tungsten, silver, stainless steel, gold, tantalum, bismuth, barium sulfate, or a similar material. The radiopaque material can be applied as layers on selected surfaces of the stent using any of a variety of well-known techniques, including cladding, bonding, adhesion, fusion, deposition, or the like.

It is further contemplated that the external surface and/or internal surface of the clip or clip element (e.g., exterior and/or interior edges or surfaces) can be coated with another material having a composition different from a primary clip material. The use of a different material to coat the surfaces can be beneficial for imparting additional properties to the clip, such as providing radiopaque characteristics, drug-reservoirs, and improved biocompatibility.

In one configuration, the external and/or internal surfaces of a clip can be coated with a biocompatible polymeric material as described herein. Such coatings can include hydrogels, hydrophilic and/or hydrophobic compounds, and polypeptides, proteins, amino acids, or the like. Specific examples can include polyethylene glycols, polyvinylpyrrolidone (PVP), polyvinylalcohol (PVA), parylene, heparin, phosphorylcholine, polytetrafluorethylene (PTFE), or the like.

The coatings can also be provided on the clip to facilitate the loading or delivery of beneficial agents or drugs, such as therapeutic agents, pharmaceuticals, and radiation therapies. Accordingly, the coating material can contain a drug or beneficial agent to improve the use of the clip. Such drugs or beneficial agents can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligionucleotides, cell permeation enhancers, and combinations thereof.

Embodiments of the clip disclosed herein can be comprised of a variety of known suitable materials (which may be deformable), including stainless steel, silver, platinum, tantalum, palladium, nickel, titanium, nitinol, nitinol having tertiary materials, niobium-tantalum alloy optionally doped with a tertiary material, cobalt-chromium alloys, or other known biocompatible materials. Such biocompatible materials can include a suitable biocompatible polymer in addition to or in place of a suitable metal. A device or member can include biodegradable or bioabsorbable materials, which can be either plastically deformable or capable of being set in the deployed configuration.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A clip for managing access to an opening in tissue, the clip comprising:
   a body having an interior edge and an exterior edge, with an upper surface and a lower surface at opposite ends of each of the interior edge and the exterior edge, the body having a first portion connected to a second portion at two fold junctions;
   the body of the clip is configured to maintain both an open position and a closed position, the body including at least one holding structure that maintains the body of the clip in the closed position, the at least one holding structure extending from the body at a location remote from the two junctions and extending over the upper surface and around a portion of the exterior edge towards the lower surface; and
   an engagement mechanism extending from the body to attach to the tissue, the body is configured to deform from a first position to a second position while the engagement mechanism is attached to the tissue.

2. The clip of claim 1, wherein the engagement mechanism comprises at least one prong that extends toward an interior of the body.

3. The clip of claim 2, wherein the at least one prong extends at an angle from the interior edge.

4. The clip of claim 2, the body including the first portion and the second portion, wherein the first portion and the second portion are joined at a fold in the body at the two junctions.

5. The clip of claim 4, wherein the first portion and the second portion are arranged in a closed position.

6. The clip of claim 4, wherein the first portion and the second portion each have a curve to accommodate the tissue.

7. The clip of claim 4, wherein the at least one prong includes a first group of prongs extending from the first portion and a second group of prongs extending from the second portion.

8. The clip of claim 2, wherein the at least one prong extends at an angle from the exterior edge.

9. The clip of claim 1, wherein the interior edge defines an interior sized to allow introduction of a medical device through the opening.

10. A clip for reducing trauma to an opening formed in tissue, the clip comprising:
    a monolithic body including a first portion, a second portion, and a fold, the fold joining the first portion and the second portion, wherein the first portion and the second portion are set in a first position and configured to deform to a second position, wherein the body is formed to maintain self-bias in the two different positions without an external bias with the first portion and the second portion of the body being generally coplanar in an open position and the body having a folded orientation in the second position, the open position being one of the two different positions and a closed position being another of the two different positions; and a plurality of prongs extending from the first portion and from the second portion, the plurality of prongs are configured to engage the tissue around the opening and attach the body to the tissue while the body is in both the first position and the second position.

11. The clip of claim 10, further comprising barbs formed on at least some of the plurality of prongs.

12. The clip of claim 10, wherein the plurality of prongs are adapted to move more towards the opening as the body deforms from the first position to the second position.

13. The clip of claim 10, wherein the first portion and the second portion are defined by an interior edge and an exterior edge, wherein the interior edge defines an interior of the body.

14. The clip of claim 13, wherein the plurality of prongs extend laterally from the interior edge.

15. The clip of claim 13, wherein the plurality of prongs extend at an angle from the interior edge.

16. The clip of claim 13, wherein the plurality of prongs extend from the exterior edge laterally or at an angle.

17. The clip of claim 13, wherein the first portion and the second portion are curved, wherein the first portion and the second portion are arranged in a generally U-shaped configuration in the first position and wherein the first portion and the second portion are substantially flat in the second position.

18. A clip for reducing trauma to an opening formed in tissue, the clip comprising:
  a body including a first portion and a second portion forming a single integral loop, the first portion being orientated at an angle with respect to the second portion with a twisted portion between first ends of the first portion and the second portion and second ends of the first portion and the second portion, the twisted portion being twisted about an axis extending along a length of the body from the first portion to the second portion; and
  a plurality of prongs extending from the first portion and from the second portion, the plurality of prongs configured to engage the tissue around the opening and attach the body to the tissue;
  wherein the second portion has a length longer than a distance between the first and second ends of the first portion, wherein the second portion can maintain a first position to keep the opening closed and maintain a second position to keep the opening open;
  wherein the second portion can maintain the first position and the second position without any external force, the second portion being received within a space defined by an inner periphery of the first portion in the first position and extending away from the space defined by the first portion in the second position.

19. A method for managing access to tissue, the method comprising:
  forming an opening in the tissue;
  placing a clip on the tissue, wherein the clip engages the tissue around the opening, the clip having a first portion and a second portion; and
  expanding the clip to a biased open position in order to introduce medical devices through an interior defined by the clip and through the opening by moving the first portion from the second portion beyond a transition movement point beyond which the clip transitions from a biased closed position to the biased open position, in the biased open position the first portion and the second portion of the clip are generally coplanar,
  then moving the first portion and the second portion of the clip towards one another beyond the transition point, wherein the clip transitions from the biased open position to the biased closed position to substantially close the opening;
  wherein the open position and the closed position of the clip each is maintained without an external bias.

20. The method of claim 19, further comprising engaging the clip in the tissue, wherein the clip comprises a plurality of prongs disposed on an interior edge of the clip or an exterior edge of the clip.

21. The method of claim 19, wherein expanding the clip further comprises preventing the opening from tearing beyond the interior of the clip.

22. A clip for managing access to tissue, the clip comprising:
  a first portion having a first free end, the first portion is configured to engage the tissue;
  a second portion having a second free end, the second portion is configured to engage the tissue, wherein the first portion and the second portion are movable between an open position and a closed position and are configured to maintain a closed position and an open position; and
  a connector that is configured to connect the first portion to the second portion, the connector encircling the first free end and the second free end as it extends from an outer surface of first portion to an outer surface of the second portion in the closed position of the clip, wherein the connector is configured to cooperate with the first end and the second end such that the first and second portions are maintained in the closed position when pushed towards each other and such that the first and second portions are maintained in the open position when pushed away from each other;
  wherein said first portion, second portion, and connector are formed as a unitary structure.

23. The clip of claim 22, wherein a transition of the first portion and the second portion between the closed position and the open position reaches a transition point such that forces keeping the first and second portions in the closed position change to keep the first and second portions in the open position.

24. The clip of claim 22, wherein the first end and the second end each include a flat portion, the flat portions configured to abut against each other when in the open position.

* * * * *